United States Patent [19]

Blum et al.

[11] Patent Number: 5,210,016
[45] Date of Patent: May 11, 1993

[54] ALLELIC ASSOCIATION OF THE HUMAN DOPAMINE (D$_2$) RECEPTOR GENE IN COMPULSIVE DISORDERS SUCH AS ALCOHOLISM

[75] Inventors: Kenneth Blum, San Antonio, Tex.; E. P. Noble, Los Angeles, Calif.; P. J. Sheridan, San Antonio, Tex.

[73] Assignees: Board of Regents, The University of Texas System, Austin, Tex.; Regents of the University of California, Berkeley, Calif.

[21] Appl. No.: 826,222

[22] Filed: Jan. 23, 1992

Related U.S. Application Data

[63] Continuation of Ser. No. 477,057, Feb. 7, 1990, abandoned.

[51] Int. Cl.$^5$ .................. C12Q 1/68; G01N 33/566
[52] U.S. Cl. ........................... 435/6; 436/501
[58] Field of Search ............... 436/501; 514/561; 435/6

[56] References Cited

U.S. PATENT DOCUMENTS 4,761,429  8/1988  Blum et al. ...................... 514/561

FOREIGN PATENT DOCUMENTS

89/05285  11/1980  PCT Int'l Appl. .

OTHER PUBLICATIONS

Byerley et al. "Molecular Genetic Studies Using D$_2$ Dopamine Receptor", May 1989.
Search Report for International Patent Application No. PCT/US91/00855, mailed Jul. 29, 1991.
Blum et al., "Allelic Association of Human Dopamine D$_2$ Receptor Gene in Alcoholism", *J. Am. Med. Assoc.*, 263(15): 2055-2060, Apr. 18, 1990.
Grandy, et al., "The human dopamine D$_2$ receptor gene is located on chromosome II at q22-q23 and identifies a TaqI RFLP", *Am. J. Human Genetics*, 45(5):778-785, Nov. 1989.
Bolos et al., "Population and pedigree studies reveal a lack of association between the dopamine D$_2$ receptor gene and alcoholism", *J. Am. Med. Assoc.*, 264(24):3156-60, Dec. 26, 1990.

*Primary Examiner*—Margaret Moskowitz
*Assistant Examiner*—Bradley L. Sisson
*Attorney, Agent, or Firm*—Arnold, White & Durkee

[57] ABSTRACT

In an important embodiment, the present invention concerns a method for diagnosing compulsive disease predisposition of an individual. The method comprises initially obtaining a DNA sample of said individual and then determining the presence or absence of a particular human D$_2$ receptor gene allele in said sample. Detection of said allele in the sample is indicative of predilection to compulsive disease. A most preferred embodiment is to detect predisposition to alcoholism, particularly because said allele has been found to be present in a majority of clinically diagnosed alcoholics. The human D$_2$ receptor gene A1 allele is most preferably detected in said sample.

6 Claims, 3 Drawing Sheets

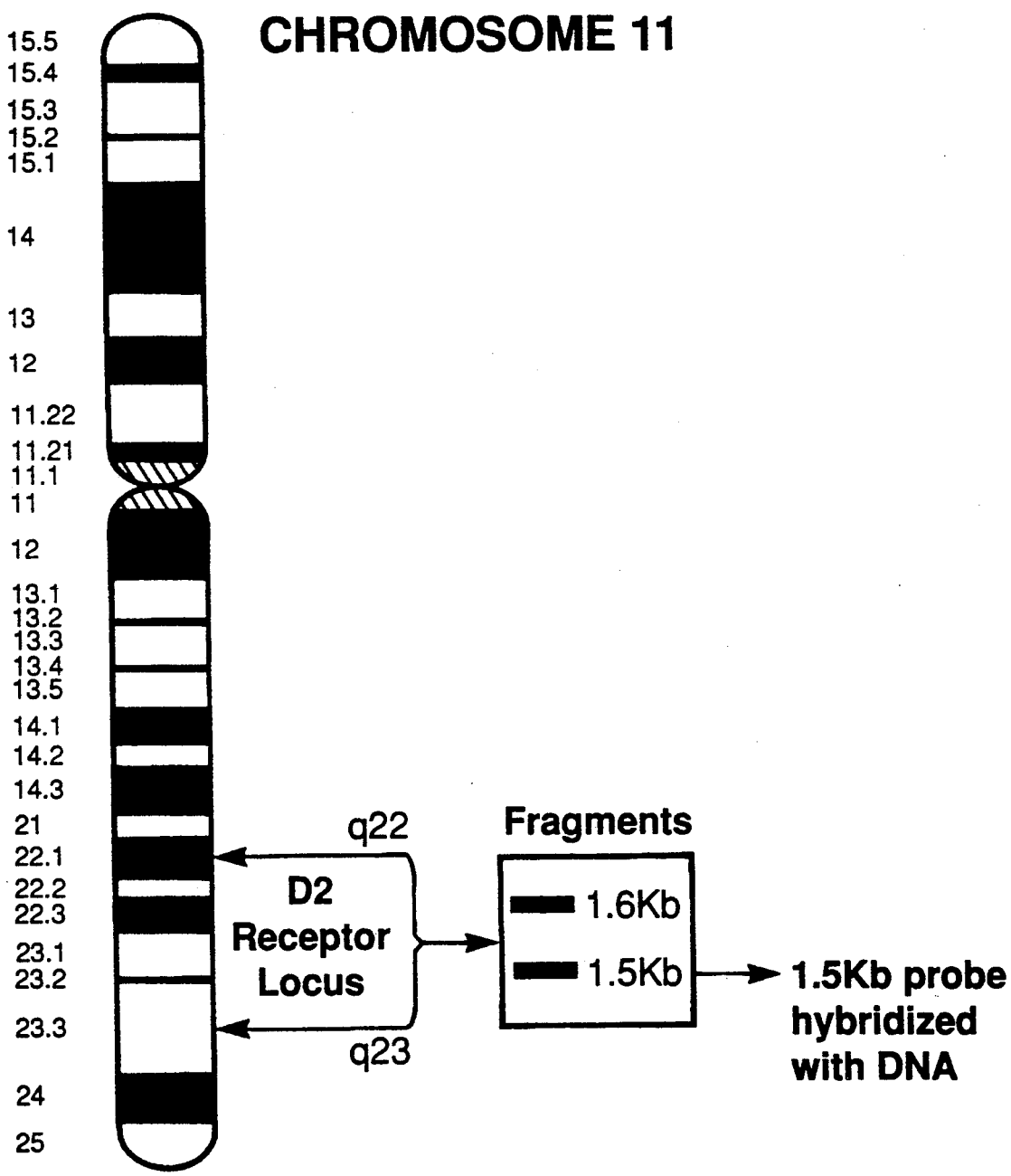

ALLELIC ASSOCIATION OF THE HUMAN DOPAMINE (D₂) RECEPTOR GENE IN COMPULSIVE DISORDERS SUCH AS ALCOHOLISM

This application is a continuation of pending application Ser. No. 07/477,057, filed Feb. 7, 1990 now abandoned.

BACKGROUND OF THE INVENTION

The present invention relates to the first molecular genetic evidence, through the use of RFLP analysis, that an allele in the human dopamine ($D_2$) receptor gene is more significantly associated with human brain tissue from alcoholics than with brain tissue obtained from nonalcoholics. The occurrence of this disease-associated polymorphism has a high predictive value in the classification of, at least, one probable subtype of alcoholics.

The identification of a genetic marker that is closely linked to alcoholism means that the gene's inheritance can be followed, leading to simple tests for diagnosing carriers and future disease victims, and potential gene therapy.

The tendency of certain individuals to display compulsive behavior patterns is well known and includes individuals with an excessive desire for substances classed as psychoactive drugs including, but not limited to alcohol, opiates, and food. Whether alcoholism is a psychiatric illness or a biological disease has been a controversial question, but there is some agreement that there are probably similar biochemical mechanisms for alcohol and opiates in terms of behavioral and pharmacological activities. (1)

Some authors believe that dopaminergic cells are implicated in the rewarding action of alcohol (23) and of opiates (2). In contrast, others (3) argue that at least alcohols/opiates and alcohol reinforcing effects are mediated primarily by nonadrenergic and not dopaminergic systems in the brain. Whether or not multiple systems exist, the question of several parallel reward mechanisms, or a very few, even one, is yet to be fully resolved. The cause and effect of compulsive behavior diseases, including alcoholism, appears to be biogenic. Regardless of the number of systems involved, the ability to identify an allelic gene segment associated with specific compulsive behavior is a significant step forward in developing predictive tests for compulsive behavior patterns.

Alcoholism is a major and devastating health problem with an unknown etiological basis. The question of whether environment or heredity is the prime determinant for the development of alcoholism continues to receive extensive attention throughout the world, and has recently involved the Supreme Court of the United States (4). However, family, twin, and adoption studies (5) are pointing to genetic factors as significant contributors to alcoholism. These studies also demonstrate that other forms of mental illness such as schizophrenia and other major psychoses are not found at higher frequencies in families of alcoholics compared with the general population. This would suggest that alcoholism is a primary disease.

Alcoholism currently is viewed as a heterogeneous entity arising from a combination of biopsychosocial factors (6). In regard to biological factors, an extensive literature reveals a wide range of potential physiological (7) and biochemical (8) markers in the risk for alcoholism. Moreover, family pedigree linkage analysis has implicated chromosomes 4, 6 and 11, but not specific gene markers, in the genetic risk for alcoholism (9).

Restriction Fragment Length Polymorphism (RFLP) offers a powerful molecular genetic tool for the direct analysis of the human genome to determine elements that provide predisposition to genetic diseases (10). This technique has been used to demonstrate a structural mutation in the gene that codes for an enzyme involved in alcohol metabolism (aldehyde dehydrogenase) which leads to the loss of this enzyme's ability to metabolize acetaldehyde. This altered gene is prevalent among Orientals (11) and may explain the well-known alcohol-flush syndrome as a protective factor in this population. However, no specific gene abnormality has been identified thus far which could regulate alcohol-seeking behavior, or is associated with alcoholism in humans.

Numerous studies indicate that, in animals, genetic control of neurotransmitter synthesis, metabolism, regulation, and receptor activity mediates reward in the meso-limbic circuitry of the brain (12), as well as drug (e.g., ethanol) - seeking behavior (13). In this regard, the dopamine₂ ($D_2$) receptor has been implicated as a prime target site in the N. accumbens and hippocampal $CA_1$ cluster cells of the brain reward system (14). Three major dopaminergic systems in the human brain have been identified. The nigrostriatal is involved in the initiation and execution of movement; the tuberoinfundibular is responsible for the regulation of peptide secretion from the pituitary; and the mesolimbic tract controls emotional stability and affect. Mediating these effects of dopamine are two receptor subtypes, $D_1$ and $D_2$, each of which is coupled to different second messenger systems. The $D_1$ receptor has been implicated in the sleep disorder, insomnia.

Important clinically relevant studies on the pharmacology of $D_2$ receptors indicated that antipsychotic drugs display high affinities for the receptor. Other work suggested that the $D_2$ receptor is involved in movement disorders, i.e., Parkinson's disease and tardive dyskinesia, tumors of the pituitary, and compulsive disease.

A cDNA encoding for rat dopamine ($D_2$) receptor has been isolated (15). This receptor has been implicated in the pathophysiology of certain diseases, including drug addiction. The same laboratory localized the receptor gene to chromsome 11 (19). Partial sequence analysis revealed that the genomic clone lambda-$hD_2G1$ (ATCC #61354 and 61355) contains the last coding exon of the $D_2$ receptor and 16.5 kb of 3-prime flanking sequence. When this clone was hybridized to human metaphase chromosomes and DNA from rodent-human hybrid cells, the data were consistent with a single human dopamine $D_2$ receptor gene which mapped to the q22-q23 region of chromosome 11. This previous work provides a research tool to begin a molecular analysis of the human $D_2$ receptor in alcoholism.

Access to sequence variation in the human genome now allows construction of genetic linkage maps through the technique of RFLPs (restriction fragment length polymorphisms). This technique provides probes which are isolated from chromosome specific phage libraries constructed to contain some portion of human DNA (16). With this tool in hand, the analysis of human gene segments is possible. The identification of an apparent gene abnormality in the tissue of alcoholics is an important advance in the art and of potential value in objectively identifying individuals who are genetically predisposed to alcoholism. The need for differential diagnosis and the ability to identify genetic predisposition has been recognized at the national level (17).

In the present invention, the DNA probe lambda-hD2G1 (ATCC #61354 and 61355) effectively visualizes the human dopamine (D2) receptor gene. This permits evaluation of polymorphisms on the gene in a region close to the gene which could modify the function of the gene as a valuable predictor of alcoholism or other compulsive disorders.

SUMMARY OF THE INVENTION

In an important embodiment, the present invention concerns a method for diagnosing compulsive disease predisposition of an individual. The method comprises initially obtaining a DNA sample of said individual and determining the presence or absence of a particular human $D_2$ receptor gene allele in said sample. Detection of said allele's presence in the sample is indicative of predilection to compulsive disease, particularly because said allele has been found to be present in a majority of clinically diagnosed victims of compulsive disease. In a most preferred embodiment, the method is used to indicate a predisposition to alcoholism, particularly because said allele has been found to be present in a majority of clinically diagnosed alcoholics. The human $D_2$ receptor gene A1 allele is most preferably detected in said sample.

The allele is readily detected by hydrolysing said DNA with Taq I restriction endonuclease and detecting the presence or absence of human $D_2$ receptor gene A1 allele in said hydrolyzed sample. This method involves separating, preferably according to their size, restriction fragments from the hydrolysate. The separated fragments are then probed with labelled lambda-hD2G1 (ATCC #61354 and 61355) or fragment thereof or with Bam H1-generated 1.3 kb fragment to specifically detect the presence or absence of human $D_2$ receptor gene A1 allele in said sample. The presence or absence of a 6.6 kb fragment in said sample, said 6.6 kb fragment being representative of the human $D_2$ receptor gene allele, is indicative of susceptibility to compulsive disease.

An object of the invention is to provide a safe and reliable method to diagnose alcohol and/or other drug risk at the prenatal and postnatal level.

The above described method may also be of value in detecting the predisposition toward other compulsive-obsessive behavior patterns including but not limited to overeating or substance abuse such as seen with nicotine, narcotics and other abused drugs.

BRIEF DESCRIPTION OF THE DRAWINGS

FIG. 1(C) schematically shows the production of the 1.5 kb probe for the dopamine $D_2$ receptor obtained from chromosome 11.

DESCRIPTION OF THE PREFERRED EMBODIMENT

Figures 1A, 1B:
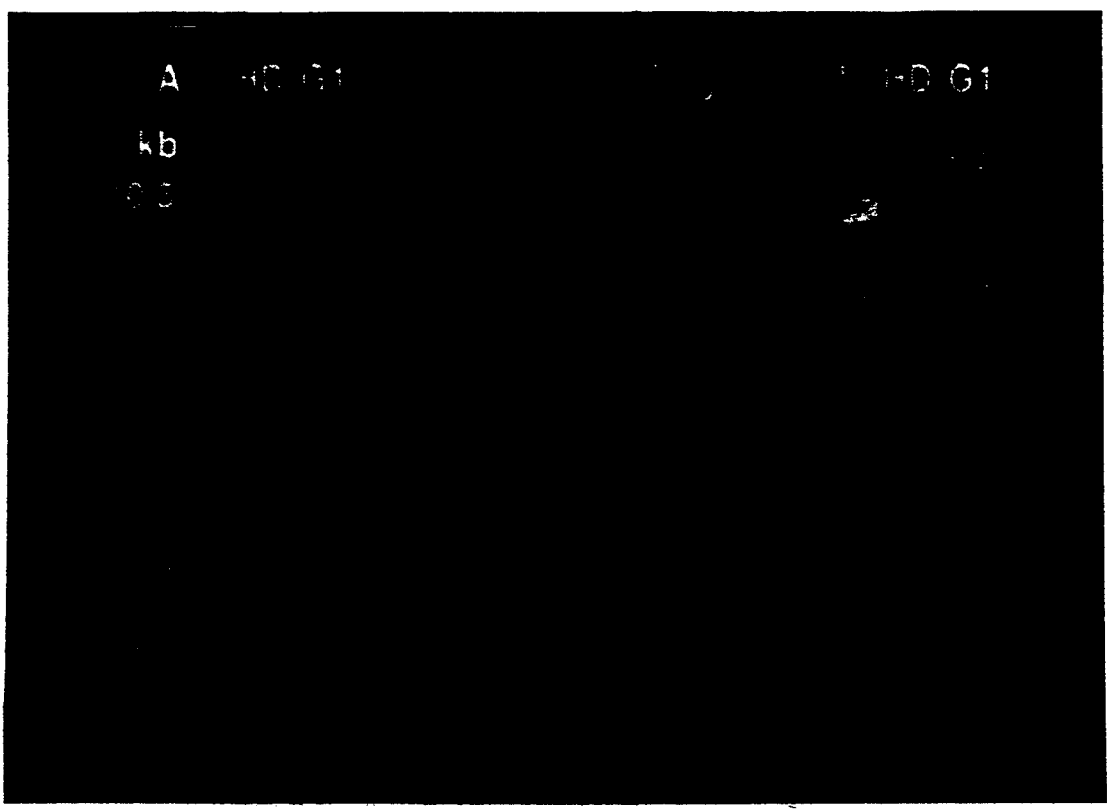
FIG. 1(A) shows the hybridization pattern of Taq I-digested DNA isolated from a heterozygous individual. The hybridization probe in the full-length lambda-hd2G1 (ATCC #61354 and 61355) which hybridizes with the 6.6 kb fragment associated with the A1 allele plus the 3.7 kb and the 2.9 kb bands associated with the A2 allele. In addition, the probe also hybridizes with two constant bands, 10.5 and 2.3 kb in length.
FIG. 1(B) shows the hybridization patterns of Taq I-digested DNA isolated from a nonalcoholic (homozygous for the A2 allele) and an alcoholic (heterozygous for the A1 and A2 alleles) individual. The hybridization probe is a 1.5 kb Bam H1 fragment isolated from lambda-hD2G1. (ATCC #61354 and 61355) Note that the smaller probe does not hybridize to the 2.9 and 2 3 kb Taq I fragments of the human dopamine $D_2$ receptor gene. Lambda-hD2G1 (ATCC #61354 and 61355) is a genomic EMBL 3 phage containing approximately 18 kb of human leukocyte DNA.

The present invention demonstrates the first allelic association, namely of the dopamine ($D_2$) receptor gene, with alcoholism. DNA, from matched alcoholic and nonalcoholic brain samples, was digested with restriction endonucleases and probed with the human $D_2$ receptor gene (lambda-hD2G1) (ATCC #61354 and 61355). The presence of the A1 allele of the dopamine ($D_2$) receptor gene correctly predicts 77% of alcoholics, and its absence is predictive of 72% of nonalcoholics. The polymorphic pattern of this receptor gene suggests that the abnormality in at least one form of alcoholism is located on the q22–q23 region of chromosome 11 with a co-dominant Mendelian mode of inheritance. The allelic association of the dopamine ($D_2$) receptor gene with alcoholism has a high predictive value in the classification of one probable alcoholic subtype. This subtype way represent a virulent form of alcoholism.

Seventy frozen brain samples were thawed and processed for high molecular weight genomic DNA. The tissue was homogenized in 0.25 M sucrose and a nuclear pellet prepared. Next the pellets were incubated at 37° C. for three hrs in 0.05% SDS and proteinase K and the DNA was extracted with phenol, followed by extraction with chloroform:isoamyl alcohol. The DNA was then spooled out, washed with ethanol, and stored in TE at 4° C. When all the DNAs were isolated, aliquots (20 ug DNA) were digested separately with four different restriction endonucleases (i.e., Taq I, Msp I, Eco RI and Pst I) at approximately two units enzyme/ ug DNA, run on agarose gels, Southern-transferred to nylon membranes, and hybridized with different DNA probes using standard methods (18). In the present experiment, the DNA samples, after digestion with the four restriction enzymes, were hybridized with a number of probes involved with either ethanol metabolism or neurotransmitter regulation of reward, including the human dopamine $D_2$ receptor gene (lambda-hD2G1) (ATCC #61354 and 61355) to determine polymorphism. A human genomic library was screened with the rat dopamine $D_2$ receptor cDNA. The human genomic library (Clonetech) in EMBL3 was prepared from normal male leukocyte DNA and screened with a nicktranslated probe containing the 1.3 kb coding portion of the rat dopamine $D_2$ receptor cDNA. One clone, lambda-$hD_2G1$, (ATCC #61354 and 61355) with an 18 kb insert was identified and characterized. This clone was found to contain the entire 3' coding exon, the polyadenylation signal, and approximately 16.4 kb of noncoding 3' sequence. Twenty ug (microgram) of the parent clone (lambda-$hD_2G1$) (ATCC #61354 and 61355) was digested with 48 units of Bam H1 for two hrs at 37° C. in Buffer C (IBI), loaded on 1% agarose gel (Sea Plaque), and run overnight at 23 volts. When digested under these conditions, several fragments were generated, including a 1.6 kb fragment and a second band of 1.5 kb, possibly made up of two 1.5 kb fragments. The 1.5 kb band was cut, heated to 68° C., diluted by a factor of three with TE buffer, and stored at 4° C. The 1.5 kb insert was labelled by random priming with $[^{32}P]$-d CTP to a specific activity of $1 \times 10^9$ cpm/ug. The diluted gel was placed in boiling water for three min and then incubated for ten min at 37° C. A 25 ul aliquot was then removed and labelled according to the oligolabeling kit (Pharmacia). The 50 ul (microliter) incubation mixture was then chromatographed through a G-50 SEPHADEX column and the eluant used for hybridization. The Taq I digested DNAs were then transferred to Nytran membranes and hybridized with the labelled insert in 50% formamide, 5 x SSC, 1 x Denhart's, 20 mM $NaH_2PO_4$, 200 g/ml of SSDNA, 0.1% SDS, 10% dextran sulfate, 0.25% dry milk, and incubated overnight at 42° C. The filters were then washed 2 x with SSC, 0.1% SDS at 55° C., and radioautographed overnight. The only endonuclease to show polymorphism with lambda-$hD_2G1$ (ATCC #61354 and 61355) was Taq I (vide infra).

In previous studies (19), where the lambda-$hD_2G1$ (ATCC #61354 and 61355) was used to probe digests of human genomic DNA, it was found that only Taq I, but not digests from 30 other endonucleases, revealed a frequent two allele RFLP. Allele A1=6.6 kb and allele A2=3.7±2.9 kb with constant bands at 10.5 and 2.3 kb. Allele frequencies were measured in 43 unrelated Caucasians and calculated to have a frequency of A1=0.24, A2=0.76. Co-dominant Mendelian inheritance was observed in four informative families with a total of 39 children. Additionally, the human dopamine ($D_2$) receptor gene was mapped on the q22-q23 region of chromosome 11 (19).

FIG. 1 illustrates the polymorphic pattern of the human dopamine ($D_2$) receptor gene. FIG. 1A depicts the polymorphic allelic pattern for the lambda-$hD_2G1$ (ATCC #61354 and 61355) gene clone. FIG. 1B shows the allelic pattern using a BamH1 1.5 kb subclone which reduced overall background and still was informative as to the presence of alleles A1 and A2. However, the smaller probe did not hybridize to the 2.9 and 2.3 kb Taq I fragments of the human dopamine ($D_2$) gene. For illustrative purposes only, the polymorphic patterns are labelled according to their highly significant allelic association with either alcoholics (A1 allele) or nonalcoholics (the absence of A1 allele), respectively labelled A1/A2 and A2/A2. The schematic production of the 1.5 kb subclone probe from chromosome 11 is shown in FIG. 1(C).

Table 1 illustrates the polymorphic pattern of the dopamine $D_2$ receptor gene with DNA obtained from alcoholic and nonalcoholic subjects following three independent hybridizations. The A1 allele is associated with 24 of 35 (69%) known alcoholics, but it associated with only 7 of 35 (20%) nonalcoholics. In contrast, the absence of the A1 allele is associated with 28 out of 35 (80%) of nonalcoholics and with only 11 of 35 (31%) alcoholics. The proportion of the presence of the A1 allele to the absence of this allele is significantly different in alcoholics as compared to nonalcoholics (Yates Chi-square corrected for continuity equals to 14.8, DF=1, P<0.001).

TABLE 1

Polymorphic pattern of the 1.5 kb fragment (lambda-$hD_2G1$) ATCCH-61354 AND 6135 of the dopamine $D_2$ receptor gene in nonalcoholic and alcoholic brain tissue.

| DNA Type | Absence of A1 Allele | Presence of A1 Allele[1] |
|---|---|---|
| Control (N = 35) | 28 (80.0)[2] | 7 (20.0) |
| Alcoholic (N = 24) | 11 (31.4) | 24 (68.6) |

[1]A1 allele = 6.6 kb
[2]Values in parenthesis represent percent of nonalcoholics or Alcoholics showing absence of the A1 allele. The proportion of the presence of the A1 allele to the absence of this allele is significantly different in alcoholics compared to nonalcoholics (Yates Chi-square corrected for continuity equals 14.8, Df = 1, P < .0001).

The race of subject populations is an important determinant in allelic patterns. Recently, Kidd et al.[3] reported that at some loci, alleles that are infrequent in Caucasians are common in other populations. As the present brains were derived from both Caucasians and Blacks, the allelic frequency of the dopamine $D_2$ receptor gene was analyzed in these two racial groups.

Table 2 illustrates the Polymorphic Pattern of the Dopamine $D_2$ Receptor Gene with DNA obtained from alcoholic and non-alcoholic Caucasians and Blacks following three independent hybridizations.

[3]K. K Kidd et al., Genome Mapping and Sequencing (Cold Spring Harbor Meeting, N.Y., 1989), pp. 66.

TABLE 2

Polymorphic Pattern of the Dopamine $D_2$ Receptor Gene (lambda-$hD_2G1$) (ATCC #61354 and 61355) in Brain Tissue of Nonalcoholics and Alcoholics

| DNA Source | Absence of A1 Allele | Presence of A1 Allele[4] |
|---|---|---|
| Nonalcoholic (N = 35) | 28 (80%)[5] | 7 (20%) |
| Alcoholic (N = 35) | 11 (31%) | 24 (69%) |
| Nonalcoholic Caucasians (N = 24) | 20 (83%) | 4 (17%) |
| Alcoholic Caucasians (N = 11) | 8 (36%) | 14 (64%) |
| Nonalcoholic Blacks (N = 11) | 8 (73%) | 3 (27%) |
| Alcoholic Blacks (N = 13) | 3 (23%) | 10 (77%) |

[4]A1 allele = 6.6 kb.
[5]Values in parentheses represent percent of nonalcoholics or alcoholics showing absence or presence of the A1 allele.

The A1 allele is found to be associated with 14 of 22 (64%) Caucasian alcoholics, but it associated with only 4 of 24 (17%) Caucasian nonalcoholics (16). The proportion of the presence of the A1 allele to the absence of the allele in Caucasian alcoholics compared to Caucasian nonalcoholics is highly significant (Yates Chi-square=8.75, DF=1, P=0.003). In Blacks, the A1 allele is associated with 10 of 13 (77%) alcoholics, but it associated with only 3 of 11 (27%) nonalcoholics. The proportion of the presence of the A1 allele to the absence of this allele is also significantly different in Black alcoholics compared to Black nonalcoholics (Yates Chi-square=5.92, DF=1, P=0.015). Thus, in the present sample, the results favor the view that A1 allelic association is based on whether or not an individual is an alcoholic, rather than the individual's racial background.

To determine the relationship between alcoholism and the A1 allele controlling for race, we used the Mantel-Hazenzel test was used. This test evaluates the relationship between two variables, while controlling for a third. Since Chi-square=14.20 with P<0.001, there is a highly significant association between alcoholism and the A1 allele was found, even after controlling for race.

In the present sample, this test also suggested that the odds ratio of finding the A1 allele in alcoholics is 8.8 times as large as that for nonalcoholics.

Figure 2:
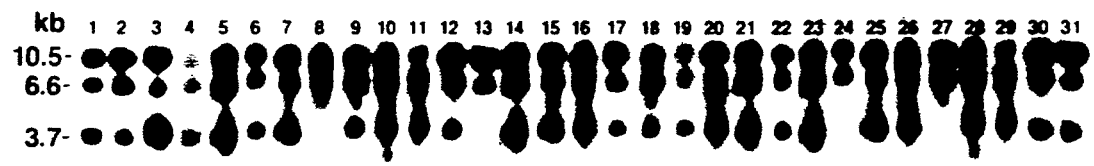
FIG. 2 shows a Southern blot analysis of human DNA from brain tissue grouped according to presence of A1 allele of the human dopamine Dz receptor gene (lambda-hD2G1) (ATCC #61354 and 61355). Predictive value in our sample size in correctly identifying alcoholics is 77% (Chi-square=9.32, DF=1, P=0.002). Note that the A2 allele (band 3.7 kb) is missing from samples 8, 13, 24, 27, and indicating that these DNAs are homozygous for the A1 allele.
Figure 3:
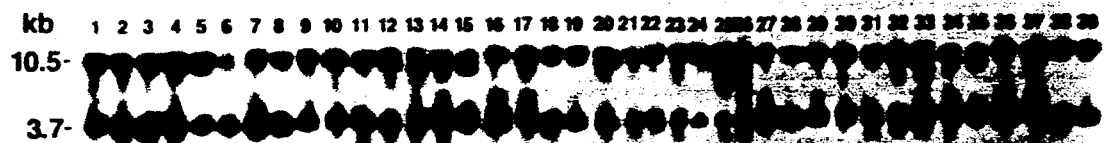
FIG. 3 shows a Southern blot analysis of human DNA from brain tissue grouped according to absence of A1 allele of the human dopamine $D_2$ receptor gene (lambda-hD2G1) (ATCC #61354 and 61355). Predictive value in correctly identifying nonalcoholics is 72% (Chi-square=7.41, DF=1, P=0.002).

FIGS. 2 and 3 show the samples grouped according to whether or not the A1 allele was present. This grouping allowed a classification of samples based on their unique allelic association with alcoholism. FIG. 2 represents 31 brain samples which possess the A1 allele (6.6). Twenty-four out of 31 DNAs that had the A1 allele were from alcoholics. This suggests, that in our sample, the predictive value of this test in correctly identifying alcoholics is 77%. FIG. 3 represents 39 brain samples which did not possess the A1 allele. Since 28 out of 39 samples did not have the A1 allele and were from nonalcoholics, this suggests that the predictive value of this test in correctly identifying nonalcoholics is 72%.

To evaluate the hypothesis that the presence or absence of the A1 allele was distributed between the alcoholic or nonalcoholic groups at other than equal probabilities, a single sample Chi-square analysis with assigned expected value of 0.50 was used. When this expected value was assigned, Chi-square analysis revealed no significant difference from the expected probability for the A1 allele in nonalcoholics (Chi-square=0.47, DF-1, P=0.50). In contrast, observed frequencies were significantly different from the expected probability of 0.25 for the A1 allele in alcoholics (Chi-square equals 35.4, DF=1, P<0.001).

To evaluate the hypothesis that the presence of the A1 allele was distributed between the alcoholic or nonalcoholic groups at other than equal probabilities, a single sample Chi-square analysis with assigned expected value of 0.25 was used to approximate the frequency of the A1 allele in the general population. When this expected value was assigned, Chi-square analysis revealed no significant difference from the expected probability for the A1 allele in nonalcoholics (Chi-square=0.47, DF=1, P=0.50). In contrast, observed frequencies were significantly different from the expected probability of 0.25 for the A1 allele in alcoholics (Chi-square=35.4, DF=1, P<0.001).

Of the total alleles in the present sample, the frequency of the A1 allele was 25% and that for the A2 allele was 75%. In the samples of nonalcoholics, A1 and A2 allelic frequencies were 13% and 87% respectively. The allelic frequencies in the samples of alcoholics were: A1 =37% and A2=63%. The frequency of the A1 allele in samples of nonalcoholics and alcoholics were significantly different (Yates Chi-square=9.75, DF=1, P=0.002).

To determine ability to correctly classify the alcoholic or nonalcoholic in this sample, according to the presence or absence of the A1 allele distributed between the two groups at a better than chance probability, a Chi-square analysis with assigned expected value of 0.50 was used. Observed values were significantly different from expected probability for the A1 allele (Chi-square=9.32, DF=1, P=0.002) and for the absence of the A1 allele (Chi-square=9.26, DF=1, P=0.002). These findings, taken together, suggest a strong allelic association of the dopamine $D_2$ receptor gene with alcoholism.

To determine the association of other putative genes with alcoholism, a number of additional candidate probes were used. Unlike lambda-hD$_2$G1, none of these probes revealed a polymorphic pattern of association with alcoholism.

Nuclear DNA was isolated from the matched brain samples as previously described for lambda-hD$_2$G1 (ATCC #61340 and 61355) probe. Twenty micrograms of DNA was digested with one of the four restriction endonucleases. The resulting DNA fragments were separated according to size by electrophoresis in 1% agarose gel, transferred to nitrocellulose membranes, fixed, and hybridized with phosphorus $^{32}$P-labelled probes. Washing of filters and autoradiography were carried out as described previously in this paper. A number of probes were employed, including alcohol dehydrogenase (pADH/3), protein kinase-C (phPKC), carboxypeptidase-A (CPA), pro-enkephalin (pHPE9), tryptophan hydroxylase (TPH479), tyrosine hydroxylase (BTH$_4$), monoamine oxidase B (MAOB), and transferrin (TF). Evaluation of the data (Table 3) revealed that none of these DNA probes utilizing four restriction endonucleases, (which endonucleases, to date, are responsible for about two-thirds of all known polymorphisms) are associated with alcoholism. The cDNA probe for alcohol dehydrogenase, an enzyme involved in the metabolism of alcohol, displays a polymorphism using Msp I, but the polymorphism is not linked to alcoholism. The cDNA probe for transferrin, a protein involved in hemoglobin lynthesis, displays polymorphism using Eco RI, but again, this polymorphism is not associated with alcoholism. Other probes used were: protein kinase-C, involved in second messenger coupling mechanisms for neuotransmitters; carboxypeptidase-A, involved in the metabolism of the opioid peptide enkephalin; pro-enkephalin, the precursor protein for the synthesis of enkephalin; the enzyme tryptophan hydroxylase, involved in the regulation of serotonin synthesis; tyrosine hydroxylase, the rate-limiting enzyme in the synthesis of dopamine; and transferrin, a protein involved in hemoglobin dynamics. This latter group of probes displayed no polymorphism with Taq I, Mso I, Eco RI, and Pst I restriction endonucleases. Thus the only probe that showed polymorphism associated with alcoholism was lambda-D$_2$GI.

TABLE 3

Evaluations of Polymorphisms of DNA Probes with Various Endonucleases

| DNA Probe | Msp I | Eco RI | Tag I | Pst I | Alcoholism Association |
|---|---|---|---|---|---|
| Alcohol Dehydrogenase (pADH/3) | yes | no | no | no | no |
| Protein Kinase-C (phPKC) | no | no | no | no | no |
| Tryptophan Hydroxylase (TPH479) | no | no | no | no | no |
| Pro-enkephalin (pHPE9) | no | no | no | no | no |
| Monoamine Oxidase (MAOB) | no | no | no | no | no |
| Carboxypeptidase A(CPA) | no | no | no | no | no |
| Transferrin(TF) | no | yes | no | no | no |
| Tyrosine Hydroxylase (BTH$_4$) | no | no | no | no | no |
| Dopamine (D$_2$) Receptor lambda-hD$_2$G1 | no | no | yes | no | yes |

Over the past three decades, research concerned with the interaction of genetic and environmental factors in the development of alcoholism shows that the risk for this behavior is determined by genetic as well as by environmental factors (20). However, the conclusion that there is a significant genetic component to alcoholism has led to the realization that individuals who are at risk of becoming alcoholic, because of inherited factors, are biologically different from individuals who have few or no inherited factors that predispose them to alcoholism. This notion has stimulated an extensive search for alcoholism genes (alcogenes) or markers to identify individuals at increased risk for alcoholism, a concept elaborated from studies of inbred strains of mice, C57 and DBA, with a differing predilection to alcohol (21).

It is possible that the polymorphism of the dopamine ($D_2$) receptor gene in the brains of alcoholics is due to alcohol-induced alteration in DNA (22); hence, the polymorphism observed might be a consequence of prolonged alcohol consumption by the alcoholic and thus represent a state marker instead of a trait marker. This possibility is unlikely, given the fairly wide prevalence (24%) of the A1 allele in the general population. Moreover, the presence of the A1 allele and its codominant Mendelian inheritance (19) in alcohol-naive children indicate that alcohol per se was not responsible for this genetic variation. It is of further interest to note that naive inbred alcoholpreferring rats show a significantly lower dopamine ($D_2$) receptor binding activity than naive alcohol-avoiding rats (23), suggesting an abnormality in this gene or in its expression. These observations support the idea that the allelic association of the dopamine ($D_2$) receptor gene, or a gene close to it, in brain tissue of alcoholics is a likely candidate trait marker for, at least, one important subtype of potential alcoholism.

Given the evidence that children of alcoholics are at a greater risk of developing alcoholism than children of nonalcoholics (24), it may be predicted that the prevalence of a candidate trait marker would be significantly greater in a population of subjects who have a positive rather than a negative family history of alcoholism.

In the present sample, derived from 70 deceased individuals, a strong association between alcoholism and the A1 of a Taq I polymorphism close to the dopamine $D_2$ receptor gene has been found. That this association prevailed in a s subsample of Caucasians and Blacks raises interesting questions about the prevalence of the A1 allele in other samples of alcoholics. It is, however, important to note that a large majority of alcoholics in the present study had experienced repeated treatment failures in their alcoholic o rehabilitation and whose cause of death was primarily attributed to the chronic damaging effects of alcohol on their bodily systems. It is possible then that the Al allele found in this study may be associated with a particular subgroup of virulent alcoholism. Besides these s molecular genetic studies, we have also carried out, in the same brain samples as above, the actual characteristics of the dopamine $D_2$ receptor using [$^3$H]spiprone (a dopamine [$D_2$] receptor antagonist ligand). The data show that the affinity of the dopamine ($D_2$) receptor ligand is significantly different in subjects having the A1 allele compared to those having the A2 allele. Thus, the evidence, put together, shows not only that a strong association is found between the A1 allele and alcoholism, but that the A1 and A2 allele express themselves in different dopamine ($D_2$) characteristics in the brain.

Unlike genetic diseases such as Huntington's chorea and cystic fibrosis (10), where a single gene is responsible for its expression, the heterogeneous nature of alcoholism may not allow for the generation of a single marker that can identify all individuals at risk.

Given that there are various subtypes of alcoholics, it would have been surprising if a 100% association was found between the A1 allele and alcoholism. In this regard, the 31% of alcoholics in this study which did not associate with the dopamine ($D_2$) receptor gene polymorphism suggests some interesting possibilities: (1) environmental (25) rather than genetic factors contributed to their alcoholism; (2) other genes may be critical for the predisposition and subsequent expression of alcohol-seeking behavior. This possibility is intriguing, since it suggests that genespecific subtypes of alcoholism could now be identified through RFLP analysis and provide the basis for multiple etiologies; and (3) there may be only partial linkage disequilibrium between the RFLP and the gene responsible for the disease. This could occur because of occasional crossover between marker and gene.

Support for alcoholism subtypes can be found in various neurochemical hypothesis, including: 1) individual differences in nerve cell membrane sensitivity to ethanol (26); 2) inherited variations in the sensitivity of sodium-potassium ATPase inhibition to ethanol (27); 3) inherited variations in neurotransmitter release and uptake systems involved in a reward cascade of events (28); 4) inherited variations in the production of abnormal amounts of tetrahydroisoquinolines (29); 5) inherited variations in the neuroadaptive mechanisms for reinforcing certain behaviors (30); and 6) inherited variation in second messenger response coupling mechanisms (31).

It is viewed as possible that the dopamine ($D_2$) receptor gene polymorphism observed herein may also be associated with predilection to other addictive diseases, such as those relating to nicotine, narcotics or other drugs.

It is believed that research dealing with the exploration of various candidate gene probes which encode elements related to the synthesis, metabolism, storage, release, and receptor activity of neurotransmitters and neuropeptides involved in brain reward might ultimately lead to multigene trait markers which can detect susceptibility of individuals with a family history of alcoholism. In the present study, a variety of other candidate probes was used which include, for example, a probe for alcohol dehydrogenase (pADH/3, ATCC #57218), an enzyme involved in the metabolism of alcohol. Although this probe displays a polymorphism using Msc I, the polymorphism is not linked to alcoholism. Thus, even if a candidate probe is thought to be involved in the action of alcohol, and if it exhibits a polymorphism, the polymorphism may not be linked to alcoholism per se. Other probes used such as the one for protein kinase-C (phPKC, ATCC #59288) involved in second messenger coupling mechanisms for neurotransmitters, exhibited no polymorphism with the restriction enzymes tested.

At this time, the present findings of an allelic association of the dopamine ($D_2$) receptor gene with alcoholism suggest that a defect in this gene, or in another gene with linkage disequilibrium with it, may cause susceptibility to, at least, one type of alcoholism. Still, this finding may hold promise for specifically focused treatment and prevention strategies. Clearly, application of the discoveries and methods described herein should have great benefit for the 28 million children of alcoholics who are potentially at risk for this disease. Finally, this research, as well as other work along similar lines, should result in the destigmatization of alcoholism, and ensure that the erroneous view of it as a moral weakness should no longer be accepted by society.

The following literature citations are incorporated in pertinent part by reference herein for the reasons cited in the above text.

REFERENCES

1. Blum et al., U.S. Pat. No. 4,761,429 (Aug. 2, 1988).
2. Wise, R.A. and Bozarth, N.A., *Pharmacol. Biochem. J. Behavior* 17, 239-243 (1982) "Action of Drugs of Abuse on Brain Reward Systems: An Update with Specific Attention to Opiates".
3. Amit, Z. and Brown, Z.W. *Pharmacol. Biochem. J. Behavior* 17, 233-238 (1982) "Actions of Drugs of Abuse on Brain Reward Systems: A Reconsideration with Specific Attention to Alcohol".
4. Supreme Court of the United States. Traynor v. Turnage, Administrator, Veterans Administration et al., and McKelvey v. Turnage, Administrator, Veterans Administration et al. (Argued Dec. 7, 1987; decided Apr. 20, 1988). Syllabus no. 86-22 and no. 86-737 (Washington, DC, 1988).
5. L. Kai, *Alcoholism in Twins: Studies on the Etiology and Sequelae of Abuse of Alcohol* (Almquist and Wiksell Publ., Stockholm, 1960); D. S. Goodwin, *Arch. Gen. Psychiatry* 25, 545 (1971); D. S. Goodwin, *ibid.* 36, 57 (1979); C. R. Cloninger, M. Bohman, S. Sigvardsson, *ibid.* 38, 861 (1981).
6. American Psychiatric Association, *Diagnostic and Statistical Manual of Mental Disorders*, 3rd edition (American Psychiatric Association, Washington, DC, 1987).
7. H. Begleiter, B. Porjesz, C. L. Chow, *Science* 211, 1064 (1981); Gabrielli et al., *Psychophysiology* 19, 404 (1982); Pollock et al., *Arch. Gen. Psychiatry* 40, 857 (1983); H. Begleiter, B. Porjesz, B. Bihari, B. Kissin, *Science* 225, 1493 (1984); S. O'Connor, V. Hesselbrock, A. Tasman, *Prog. Neuropsychopharmacol. Biol. Psychiatry* 10, 211 (1986); S. C Whipple, E. S. Parker, E. P. Noble, *J. Stud. Alcohol* 49, 240 (1988).
8. S. Takahashi, N. Tani, H. Yamane, *Folia Psychiat. Neurol. Jpn.* 30, 455 (1976); A. Wiberg, C. G. Gottfried, L. Oreland, *Med. Biol.* 55, 181 (1977); J. L. Sullivan, J. O. Cavenar, Jr., A.A. Maltbie, P. Lister, W.W.K. Zung, *Biol. Psychiatry* 14. 385 (1979); C. J. Fowler, K. F. Tipton, A. V. P. MacKay, M. B. H. Youdim, *Neuroscience* 7, 1577 (1982); L. Oreland et al., *J. Neural Transm.* 56, 73 (1983); G. Alexopoulos, K. W. Lieberman, R. J. Frances, *Am. J. Psychiatry* 140, 1501 (1983); A. L. von Knorring, M. Bohman, L. von Knorring, L. Oreland, *Acta Psychiat. Scand.* 72, 51 (1985); I. Diamond, B. Wrubel, W. Estrin, A. Gordon, *Proc. Natl. Acad. Sci. USA* 84, 1413 (1987); B. Tabakoff et al., *N. Eng. J. Med.* 318, 134 (1988); D. Mochly-Rosen et al., *Nature* 333, 848 (1988).
9. S. Hill, D. W. Goodwin, R. Cadoret, C. K. Osterland, S. M. Doner, *J. Stud. Alcohol* 36, 981 (1975); Y. Shigeta et al., *Pharmacol. Biochem. Behav.* 13 (Suppl. 1), 89 (1980); S. Y. Hill, J. Armstrong, S. R. Steinhauer, T. Baughman, J. Zubin, *Alcoholism* (NY) 11, 345 (1987).
10. Y. W. Kan., A. M. Dosy, *Proc. Natl. Acad. Sci. USA* 75, 5631 (1978); J. S. Gusella et al., *Nature* 306, 234 (1983); D. S. Gerhard et al., *Am. J. Hum. Genet.* 36, 3S (1984); M. J. M. Saraiva, P. P. Costa, D. S. Goodman, *Neurology* 36, 1413 (1986); R. J. Bartlett et al., *Science* 235, 1648 (1987); P. H. St. George-Hyslop et al., al., *ibid*, 885; M. Barrow et al., *Nature* 326, 289 (1987); J. M. Rommens et al., *Science* 245, 1059 (1989); J. R. Riordan et al., *ibid*, 1066; B. Kerem et al., *ibid*, 1073.
11. W. F. Bosron, T-K. Li, *Biochem. Biophys. Res. Commun.* 91, 1549 (1979); D. P. Agarwal, S. Harada, H. W. Goedde, *Alcoholism* (NY) 5, 12 (1981); W. F. Bosron, L. J. Magnes, T-K. Li, *Biochem. Genet.* 21, 735 (1983); A. Yoshida, G. Wang, V. Dave, *Am. J. Hum. Genet.* 35, 1107 (1983); A. Yoshida, I-Y. Huang, M. Ikawa, *Proc. Natl. Acad. Sci. USA* 81, 258 (1984); H. W. Goedde, D. P. Agarwal, in *Genetics of Alcoholism*, H. W. Goedde, D. P. Agarwal, Eds. (Alan Liss, NY, 1987), pp. 3-20.
12. A. S. Lippa, S. M. Antelman, A. E. Fisher, D. R. Canfield, *Pharmacol. Biochem. Behav.* 1, 23 (1973); L. Ahtee, K. Eriksson, *Acta Physiol. Scand.* 93, 563 (1975); M. D. Dibner, N. R. Zahniser, B. B. Wolfe, R. A. Rabin, P. B. Molinoff, *Pharmacol. Biochem. Behav.* 12, 509 (1980); R. A. Wise, ibid. 13 (Suppl. 1), 213 (1980); M. L. Barbaccia, A. Reggiani, P.F. Spano, M. Trabucchi, *Psychocharmacology* 74, 260 (1981).
13. M. K. Ticku, T. Burch, *J. Neurochem.* 34, 417 (1980); S. F. A. Elston, K. Blum, L. DeLallo, A. H. Briggs, *Pharmacol. Biochem. Behav.* 16, 13 (1982); K. Blum, S. F. A. Elston, L. DeLallo, A. H. Briggs, J. E. Wallace, *Proc. Natl. Acad. Sci. USA* 80, 6510 (1983); K. Blum, A. H. Briggs, J. E. Wallace, C. W. Hall, M. C. Trachtenberg, *Experientia* 43, 408 (1986); C. Gianoulakis, A. Gupta, *Life Sci.* 39, 2315 (1986); K. Blum, H. Topel, *Funct. Neurol.* 1, 71 (1986); J. M. Murphy, W. J. McBride, L. Lumeng, T-K. Li, *Pharmacol. Biochem. Behav.* 26. 389 (1987); J. M. Murphy et al., *Alcohol* 5, 283 (1988).
14. S. Liljequist, *Acta Pharmacol. Toxicol.* 43, 19 (1978); S. A. Newlin, J. Mancillas-Trevino, F. E. Bloom, *Brain Res.* 209, 113 (1981); G. Mereu, F. Fadda, G. L. Gessa, *Brain Res.* 292, 63 (1984); L. Stein, J. Belluzzi, *Clin. Neuropharmacol.* 9 (suppl. 4), 205 (1986); S. Govoni et al., *Brain Res.* 381, 138 (1986); P. Valverius, P. L. Hoffman, B. Tabakoff, *J. Neurochem.* 52, 492 (1989); F. Fadda, E. Mosca, G. Columbo, G. L. Gessa, *Life Sci.* 44, 281 (1989).
15. Bunzow et al. Nature, 336. 783-787 (1988) "Cloning and Expression of a Rat ($D_2$) Dopamine Receptor cDNA".
16. Maslen, et al. Genomics, 2, 66 (1988).
17. Tabakoff, et al. Public Health Reports, Vol. 103(6), 690-698 (1988) "Genetics and Biological Markers of Risk for Alcoholism".
18. T. Maniatis, E. F. Fritsch, J. Sambrook, Eds., *Molecular Cloning. A Laboratory Manual* (Cold Spring Harbor Laboratory, Cold Spring Harbor, N.Y., 1982).
19. D. K. Grandy et al., *Am. J. Hum. Genet.* (1989, in press).
20. C. R. Cloninger, T-K. Li, *Alcoholism: An Inherited Disease* (U.S. Government Printing Office, Washington, DC, 1985), DHHS Publ. No. (ADM)85-1426; C. R. Cloninger, Psychiat. Dev. 3, 167 (1986).
21. R. D. Myers, in *Aldehyde Adducts in Alcoholism*, M. A. Collins, Ed. (Alan R. Liss, NY, 1985), pp. 201-220.
22. G. Obe, H. Ristow, J. Herha, in *Biochemistry and Pharmacology of Ethanol: Vol. I*, E. Majchrowicz, E. P. Noble, Eds. (Plenum Press, NY, 1979), pp. 659-676.

23. E. R. Korpi, J. D. Sinclair, O. Malminen, *Pharmacol. Toxicol.* 61, 94 (1987).
24. M. A. Schuckit, in *Psychiatry Update: Vol. III*, L. Grinspoon, Ed. (American Psychiatric Press, Washington, DC, 1986), pp. 320–328.
25. Blocking of dopamine ($D_2$) receptors reduces rewardseeking behaviors in animals (C. R. Gallistel, A. J. Davis, *Pharmacol. Biochem. Behav.* 19, 867 [1983]). Acute alcohol administration increases pleasureful behavior by releasing dopamine (A. Imperato, G. Chiara, *J. Pharmacol. Exp. Ther.* 239, 219 [1986]) through stimulation of dopaminergic neurons in the ventral tegmental area of the brain (G. L. Gessa, F. Muntoni, M. Collu, L. Vargiu, G. Mereu, *Brain Res.* 348, 201 [2985]). However, chronic ethanol ingestion reduces the responsiveness and number of dopamine ($D_2$) receptors in striatal membranes of rats (L. Lucchi, R. M. Moresco, S. Govoni, M. Trabucci, *Brain Res.* 449, 337 [1988]). The consequence of decreased activity of this reward system may lead to a compensatory increase in alcohol-seeking behavior. This could be one nongenetic mechanism for developing alcoholism.
26. D. B. Goldstein, J. H. Chin, R. C. Lyon, *Proc. Natl. Acad. Sci. USA* 79, 4231 (1982).
27. Y. Israel, H. Kalant, I. Lanfer, *Biochem. Pharmacol.* 14, 1803 (1965); A. L. Swann, *J. Pharmacol. Exp. Ther.* 232. 475 (1985); P. T. Nhamburo, B. P. Salafsky, B. Tabakoff, P. L. Hoffman, *Biochem. Pharmacol.* 36, 2027 (1987).
28. F. E. Bloom, *Advanc. Pharmacol. Ther.* 2, 205 (1979); K. Blum, A. H. Briggs, M. C. Trachtenberg, *Experientia* 45, 444 (1989); K. Blum, *Integr. Psychiat.* 6, 199 (1989).
29. G. Siggins, T. Berger, E. D. French, T. Shier, F. E. Bloom, *Proc. Clin. Biol. Res.* 90, 275 (1982); R. D. Myers, *Experientia* 45, 436 (1989); R. D. Myers, T. H. Privette, *Brain Res. Bull.* 22, 899 (1989); B. Faraj, V. M. Camp, D. C. Davis, J. D. Lenton, K. Kutner, *Alcoholism* 13, 155 (1989).
30. C. R. Cloninger, M. Bohman, S. Sigvardsson, *Arch. Gen. Psychiatry* 38, 861 (1981); C. R. Cloninger, *Science* 236, 410 (1987); D. W. Goodwin, *J. Stud. on Alc.* 50, 397 (1989).
31. J. H. Allison, T. J. Cicero, *J. Pharmacol. Exp. Ther.* 13, 24 (1980); P. L Hoffman, F. Moses, G. R. Luthin, B. Tabakoff, *Mol. Pharmacol.* 30, 13 (1986); G. Y. Sun, H-M. Huang, R. Chandrasekhar, D. Z. Lee, A. Y. Sun, *J. Neurochem.* 48, 974 (1987); T. Ritchie, H-S. Kim, R. Cole, J. de Vellis, E. P. Noble, *Alcohol* 5, 183 (1988); D. H. Ross, *Experientia* 45, 407 (1989).

Changes may be made in the processes of the invention described herein without departing from the concept and scope of the invention as defined in the following claims.

What is claimed is:

1. A method of detecting a genetic potential susceptibility to alcoholism in a human subject, comprising:
   obtaining DNA from a subject; and
   detecting, in said DNA, a human dopamine $D_2$ receptor gene A1 allele, wherein said A1 allele indicates a potential susceptibility to alcoholism.

2. The method of claim 1 wherein detecting a human dopamine $D_2$ receptor gene $A_1$ allele comprises:
   subjecting said DNA of said subject to digestion by TaqI restriction enzyme;
   separating resultant DNA fragments;
   hybridizing said separated DNA fragments to a labeled recombinant phage $\lambda$-$hD_2G1$ or a fragment thereof specifically binding the 6.6 kb A1 allele of the human dopamine $D_2$ receptor;
   determining the presence of said A1 allele of the human dopamine $D_2$ receptor.

3. The method of claim 2 wherein the fragment of recombinant phage $\lambda$-$hD_2G1$ is a BamHI fragment having an about 1.3 kb size.

4. A method of detecting a genetic potential susceptibility to alcoholism in a human subject, comprising:
   obtaining DNA from said subject;
   subjecting said DNA of said subject to digestion by TaqI restriction enzyme;
   separating resultant DNA fragments;
   hybridizing said separated DNA fragments to a labeled recombinant phage $\lambda$-$hD_2G1$ or a fragment thereof specifically binding the 6.6 kb A1 allele of the human dopamine $D_2$ receptor;
   determining the presence of said A1 allele of the human dopamine $D_2$ receptor.

5. The method of claim 4 wherein the fragment of recombinant phage $\lambda$-$hD_2G1$ is a BamHI fragment having an about 1.3 kb size.

6. The method of claim 2 or 4 wherein the DNA fragments are separated by electrophoresis according to size.

* * * * *

UNITED STATES PATENT AND TRADEMARK OFFICE
CERTIFICATE OF CORRECTION

PATENT NO. : 5,210,016

DATED : May 11, 1993

INVENTOR(S) : Kenneth Blum, E.P. Noble and P.J. Sheridan

It is certified that error appears in the above-indentified patent and that said Letters Patent is hereby corrected as shown below:

```
In claim 2, column 14, line 17, please delete "A₁" and insert
therefor --A1--.
```

Signed and Sealed this

Twenty-fifth Day of January, 1994

Attest:

BRUCE LEHMAN

*Attesting Officer*   *Commissioner of Patents and Trademarks*